United States Patent [19]

Habeeb et al.

[11] Patent Number: 4,867,892

[45] Date of Patent: Sep. 19, 1989

[54] ANTIWEAR ADDITIVES FOR LUBRICATING OILS

[75] Inventors: Jacob J. Habeeb, Westfield, N.J.; Christopher J. May, Sarnia, Canada

[73] Assignee: Exxon Research and Engineering Company, Florham Park, N.J.

[21] Appl. No.: 138,217

[22] Filed: Dec. 28, 1987

[51] Int. Cl.$^4$ ............................................ C10M 135/08
[52] U.S. Cl. ................................... 252/42.7; 252/46.4
[58] Field of Search ........................ 252/46.4, 35, 42.7

[56] References Cited

U.S. PATENT DOCUMENTS

| | | | |
|---|---|---|---|
| 3,069,357 | 12/1962 | Chesluk et al. | 252/46.4 |
| 3,764,534 | 10/1973 | Blejean et al. | 252/46.4 |
| 4,104,310 | 8/1978 | Angstadt | 568/311 |
| 4,228,217 | 10/1980 | Baur | 252/35 |
| 4,263,152 | 4/1981 | King et al. | 252/46.4 |
| 4,308,154 | 12/1981 | Clason et al. | 252/35 |
| 4,618,722 | 10/1986 | Drake | 568/38 |

Primary Examiner—William R. Dixon, Jr.
Assistant Examiner—Ellen M. McAvoy
Attorney, Agent, or Firm—John W. Ditsler

[57] ABSTRACT

Metal palmitates have been found to give excellent antiwear properties to an engine lubricating oil. They are particularly effective when used in a complex with dimethyl sulfoxide.

30 Claims, 2 Drawing Sheets

ANTIWEAR ADDITIVES FOR LUBRICATING OILS

BACKGROUND OF THE INVENTION

1. Field of the Invention

The present invention relates to metal palmitate-dimethyl sulfoxide complexes and their method of preparation. The invention also concerns the use of metal palmitates, alone or complexed with dimethyl sulfoxide, as an antiwear additive in lubricating oils.

2. Description of Related Art

Metal complexes prepared from dialkyl sulfoxides have been known for a number of years (see "Complexes of Sulfoxides. I. Octahedral Complexes of Manganese (II), Iron (II), Cobalt (II), Nickel (II), and Zinc (II)," Currier, W. F. and Weber, J. H. *Inoro. Chem.* 6, 1539 (1967); and "Preparation of Several Sulfoxide Complexes with Group IV Organometallic Compounds," Langer, H.G. and Blut, A. H., *J. Oroanometal. Chem.* 5(3), 288-91 (1966)). For example, U.S. Pat. No. 4,104,310 discloses the preparation of a catalytically active complex from dimethyl sulfoxide and metal salts in which the possible organic anions include acetate, tartrate, benzoate or oxalate groups. As another example, U.S. Pat. No. 4,618,722 discloses the preparation of lubricant additives from a metal carboxylate and a hydrocarbyl halide in the presence of dimethyl sulfoxide (as the reaction solvent) to yield dihydrocarbyl sulfides.

However, none of the foregoing references disclose metal palmitate-dimethyl sulfoxide complexes, their method of preparation and use as antiwear additives in engine lubricating oils.

SUMMARY OF THE INVENTION

Now according to the present invention, it has been discovered that an engine lubricating oil containing a metal palmitate-dimethyl sulfoxide complex has effective antiwear properties. A method of preparing said complex is also disclosed. Further, the present invention contemplates a method for improving the antiwear properties of an engine lubricating oil by adding at least one metal palmitate, alone or complexed with said dimethyl sulfoxide, to a lubricating oil basestock.

DETAILED DESCRIPTION OF THE INVENTION

Figure 1:
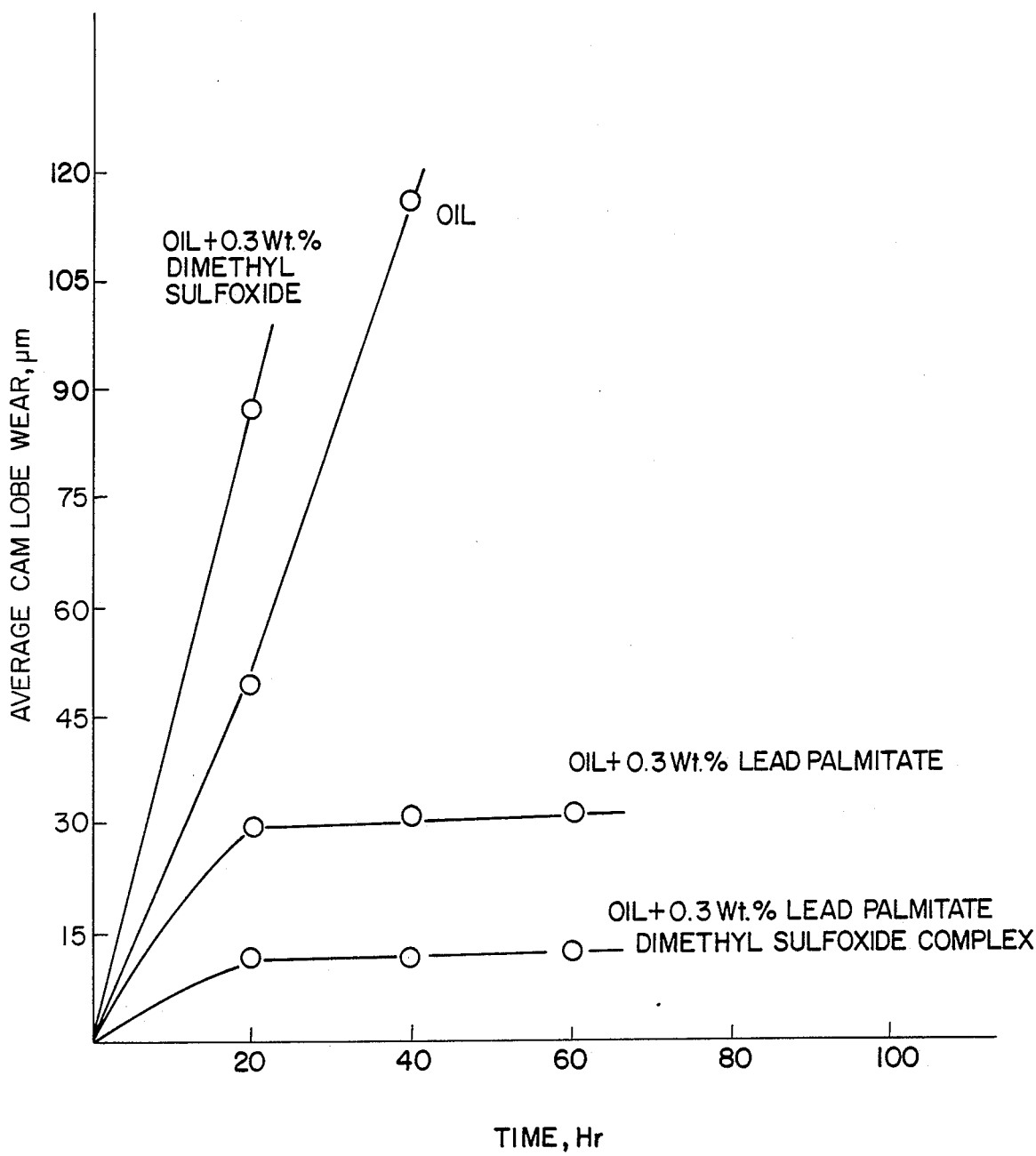
FIG. 1 is a plot of average cam lobe wear versus time which shows that lead palmitate and a lead palmitate-dimethyl sulfoxide complex are effective antiwear additives.

In one embodiment, the present invention relates to an engine lubricating oil composition containing a metal palmitate-dimethyl sulfoxide complex which has improved antiwear properties. In another embodiment, the present invention concerns a method of improving the antiwear properties of an engine lubricating oil which comprises adding at least one metal palmitate or at least one metal palmitate-dimethyl sulfoxide complex to said oil. In still another embodiment, the present invention relates to the preparation of said metal palmitate-dimethyl sulfoxide complexes.

The metal palmitate used in the present invention will comprise a metal selected from the group consisting of Groups IB, IIB, IVB, VB, VIB, VIIB and VIIIB of the Periodic Table and mixtures thereof. Preferred metals are copper, lead, molybdenum, nickel, tin and zinc, with lead and tin be particularly preferred. Several of these metal palmitates are commercially available. As such, their method of manufacture is well known to those skilled in the art.

The metal palmitate-dimethyl sulfoxide complex may be prepared by heating metal palmitate with an excess of dimethyl sulfoxide (DMSO) at a temperature between about 50° to about 130° C. (preferably from about 90° to about 115° C.) for a period of time ranging from about 1 to about 4 hours (preferably from about 2 to about 3 hours). The mixture is then cooled to a temperature between about 10° and about 25° C. and the metal palmitate-DMSO complex recovered by one or more separation techniques; e.g. filtration.

The amount of metal palmitate (or metal palmitate-dimethyl sulfoxide complex) present in the engine lubricating oil of the present invention will vary depending upon the degree of wear reduction desired, the amount of other antiwear additives present (if any), the specific operating parameters used and the specific application of the oil. In general, the amount need only be that which is effective in imparting antiwear properties to said oil. Typically, however, the amount should range between about 0.05 and about 1.5 wt. % (preferably between about 0.1 and about 1.0 wt. %) although larger amounts could be used if desired.

The engine lubricating oil to which the metal palmitate (or metal palmitate-DMSO complex) is added comprises a major amount of a lubricating basestock (or base oil) and a minor amount of the metal palmitate or metal palmitate-DMSO complex. The basestock may include liquid hydrocarbons such as the mineral lubricating oils, synthetic lubricating oils or mixtures thereof. The mineral oils may include paraffinic, naphthenic as well s aromatic components. The synthetic oils may include diester oils such as di(2-ethylhexyl) sebacate, azelate and adipate; complex ester oils such as those formed from dicarboxylic acids, glycols and either monobasic acids or monohydric alcohols; polyolester oils such as esters of pentaerythritol and/or trimethylol propane; and other synthetic oils (including synthetic hydrocarbons) known to the art.

In addition to the metal palmitate or metal palmitate-DMSO complex, other additives known in the art may be added to the oil composition of the present invention to form a fully formulated engine oil. Such additives include dispersants, other antiwear agents, antioxidants, corrosion inhibitors, detergents, pour point depressants, extreme pressure additives, viscosity index improvers and the like. These additives are typically disclosed, for example, in "Lubricant Additives" by C. V. Smalheer and R. Kennedy Smith, 1967, pp. 1-11 and in U.S. Pat. No. 4,105,571, the disclosures of which are incorporated herein by reference.

Although the embodiments of the present invention have been described with respect to metal palmitates alone or complexed with DMSO, the embodiments would be equally applicable to other metal salts of fatty acids such as metal laurates, metal oleates and metal stearates alone or complexed with DMSO. This may be seen from the general formula for such metal salts shown below:

$$\left[ R-\overset{O}{\underset{\|}{C}}-O \right]_n M$$

wherein M is one of the metals described above, n is the oxidation state of said metal and R is a saturated or unsaturated alkyl group having at least 10 carbon atoms. Thus, the number of carbon atoms in R will be 11 for metal laurates, 17 for metal oleates, 15 for metal palmitates and 17 for metal stearates. At least 10 carbon atoms are required to ensure solubility of the metal salts in the lubricating oil.

The present invention may be further understood by reference to the following examples which are not intended to restrict the scope of the claims appended hereto.

Experimental Procedure

Valve train wear tests were performed in the following examples utilizing a Ford 2.3 liter engine with the pistons and connecting rods removed. The engine was driven with an 11.2 KW (15 horsepower) DC drive motor through a 1.2 timing belt drive. The engine was equipped with Oldsmobile valve springs (146.5–148.3 KG) to increase the load between the cam lobes and the followers. Both oil and coolant circulation were accomplished by use of the engine mounted pumps. All test runs were made at 90° C. oil temperature, 90° C. coolant temperature, approximately 331 kPa oil pressure and an engine speed of 1,000 plus or minus 6 rpm.

During operation, wear occurs on the lobes of the cam shaft and followers due to the sliding contact. As in the sequence V-D test described in ASTM Test No. STP 315H-Part 3, the disclosure of which is incorporated herein by reference, wear is defined as the reduction of the head-to-toe measurement at the point of maximum lift on the cam shaft. A pre-measured cam shaft is measured at various time intervals during the test to establish the reduction in the head-to-toe distance, i.e. the degree of wear. The tests were conducted with a commercially available lubricating oil from which the anti-wear additive had been removed and to which t-butyl hydroperoxide (90 millimoles/1000 g oil) was added to simulate actual used oil conditions.

EXAMPLE 1—Preparation of Lead and Tin Palmitate-DMSO Complexes

In this example, 20 g of lead palmitable salt was added to 100 ml of dimethyl sulfoxide in a 250 ml three neck round bottom flask fitted with a water cooed condenser and a thermometer. The mixture was stirred for two hours at 110° C. After cooling to room temperature, the mixture was filtered and the solid was dried in vacuo.

The resulting product was a lead palmitate-DMSO complex.

The same procedure was repeated using tin palmitate to form a tin palmitate-DMSO complex.

EXAMPLE 2—Oil Without Additive

An engine test was performed using the lubricating oil specified above. The engine was run for only 40 hours to prevent engine seizure due to high wear which had been detected after 20 hours of operation. The average cam lobe wear was 65 micrometers(um) and 137 um after 20 and 40 hours, respectively.

EXAMPLE 3—Oil with DMSO

A test similar to that described in Example 1 was run in which the lube oil contained 0.3 weight percent of DMSO. The test was run for only 20 hours due to high wear after which the cam lobe was measured. The average cam lobe wear was 86 um after 20 hours.

EXAMPLE 4—Oil with Lead Palmitate

A test similar to that of Example 1 was conducted but in this test 0.3 weight percent of lead palmitate was added to the lube oil. The average cam lobe wear was 30 um, 30 um and 31 um after 20, 40 and 60 hours of testing, respectively.

EXAMPLE 5—Oil with Lead Palmitate-DMSO Complex

Another test was conducted in a manner similar to that of Example 1. However, in this test the lube oil had added thereto 0.3 weight percent of the lead palmitate-DMSO complex prepared in Example 1. The average cam lobe wear was only 10 um, 11 um and 11 um after 20, 40 and 60 hours of testing, respectively.

EXAMPLE 6—Oil with Tin Palmitate

A test similar to that of Example 3 was conducted but in this test 0.7 weight percent of tin palmitate was added to the lube oil. The average cam lobe wear was 8 um, 18 um, and 23 um after 20, 40 and 60 hours, respectively.

EXAMPLE 7—Oil with Tin Palmitate-DMSO Complex

Another test was conducted in a manner similar to that of Example 4. However, in this test the lube oil had added thereto 0.7 weight percent tin palmitate-DMSO complex. The average cam lobe wear was only 7 um, 9 um and 10 um after 20, 40 and 60 hours of testing, respectively.

Figure 2:
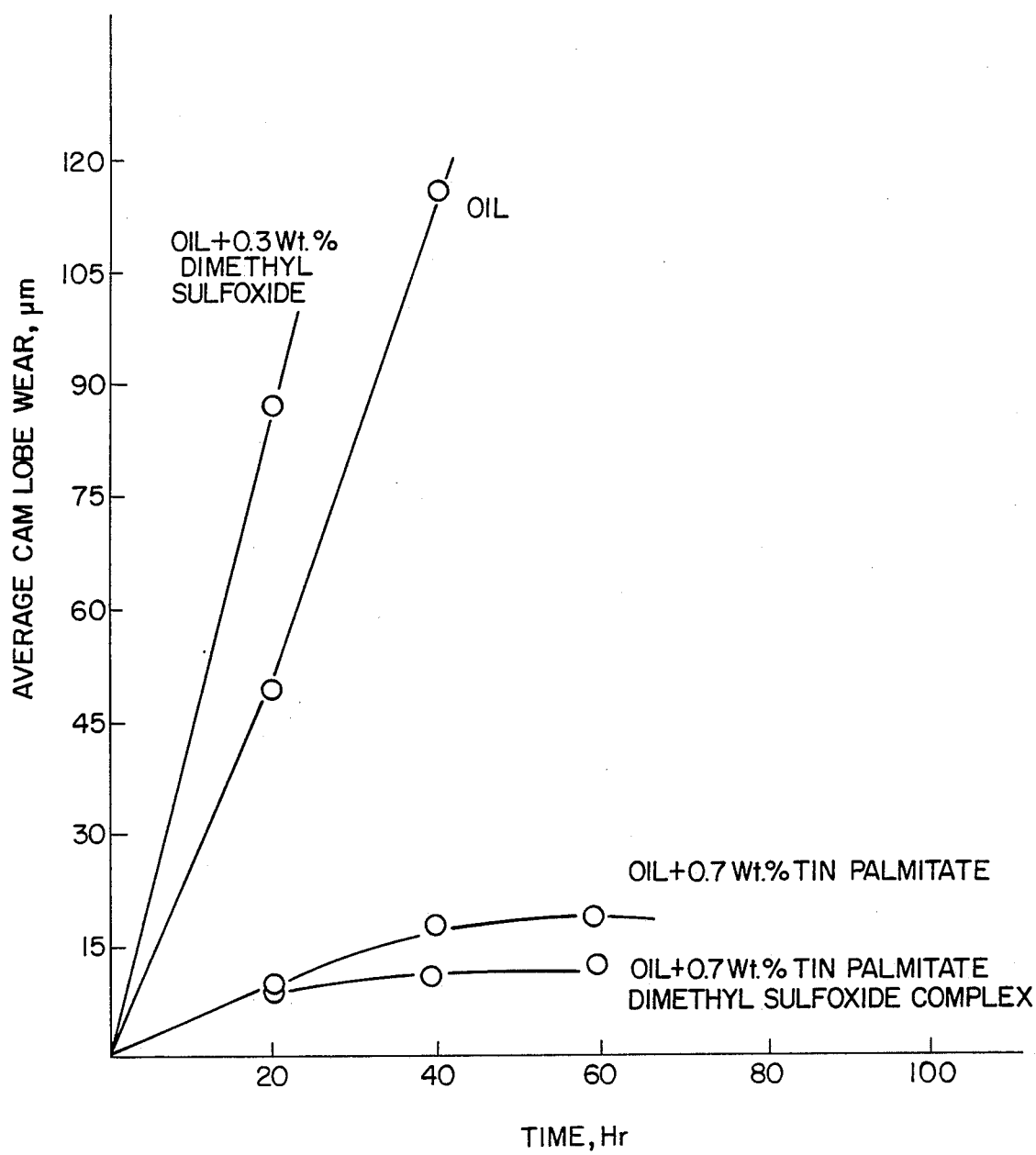
FIG. 2 is a plot of average cam lobe wear versus time which shows that tin palmitate and a tin palmitate-dimethyl sulfoxide complex are effective antiwear additives.

The data obtained in Examples 2–7 are summarized in Table 1 and shown in FIGS. 1 and 2.

TABLE 1

| Example | Additive Concentration (wt. %) | | | | Average Cam Lobe Wear (um) | | |
|---|---|---|---|---|---|---|---|
| | DMSO | Pb Palmitate | Sn Palmitate | MP—DMSO | 20 hr | 40 hr | 60 hr |
| 2 | — | — | — | — | 65 | 137 | — |
| 3 | 0.3 | — | — | — | 86 | — | — |
| 4 | — | 0.3 | — | — | 30 | 30 | 31 |
| 5 | — | — | — | 0.3 | 10 | 11 | 11 |
| 6 | — | — | 0.7 | — | 8 | 18 | 23 |
| 7 | — | — | — | 0.7 | 7 | 9 | 10 |

The data in Table 1 as illustrated in FIGS. 1 and 2 show that the use of metal palmitates result in reduced cam lobe wear, with even better results being obtained using a metal palmitate-DMSO complex.

What is claimed is:

1. An engine lubricating oil composition which comprises a major amount of a lubricating oil basestock and a minor amount of at least one metal salt of a fatty acid that is complexed with dimethyl sulfoxide, wherein said metal is selected from the group consisting of Groups IB, IIB, IVB, VIB, VIIB, VIIIB and mixtures thereof.

2. The composition of claim 1 wherein said metal is selected from the group consisting of copper, lead, molybdenum, nickel, tin, zinc and mixtures thereof.

3. The composition of claim 2 wherein said metal is selected from the group consisting of lead, tin and mixtures thereof.

4. The composition of claim 1 wherein from about 0.05 to about 1.5 wt. % of said metal salt of a fatty acid is present in said engine lubricating oil.

5. The composition of claim 1 wherein the said metal salt of a fatty acid has at least 11 carbon atoms.

6. An engine lubricating oil composition which comprises a major amount of a lubricating oil basestock and a minor amount of at least one metal salt of a fatty acid that is complexed with dimethyl sulfoxide, wherein said metal salt of a fatty acid is selected from the group consisting of metal laurates, metal oleates, metal palmitates or metal stearates and said metal is selected from the group consisting of Groups IB, IIB, IVB, VIB, VIIB, VIIIB and mixtures thereof.

7. The composition of claim 6 wherein said metal salt of a fatty acid comprises a metal palmitate.

8. The composition of claim 7 wherein said metal is selected from the group consisting of copper, lead, molybdenum, nickel, tin, zinc and mixtures thereof.

9. The composition of claim 8 wherein said metal is selected from the group consisting of lead, tin and mixtures thereof.

10. The composition of claim 6 wherein from about 0.05 to about 1.5 wt. % of said metal salt of a fatty acid is present in said engine lubricating oil.

11. The composition of claim 6 wherein said metal salt of a fatty acid has at least 11 carbon atoms.

12. A method of improving the antiwear properties of an engine lubricating oil basestock which comprises adding an effective amount of at least one metal salt of a fatty acid that is complexed with dimethyl sulfoxide to said basestock, wherein said metal is selected from the group consisting of Groups IB, IIB, VIB, VIIB, VIIIB and mixtures thereof.

13. The method of claim 12 wherein said metal salt of a fatty acid is selected from the group consisting of metal laurates, metal oleates, metal palmitates or metal stearates.

14. The method of claim 13 wherein said metal salt of a fatty acid comprises a metal palmitate.

15. The method of claim 14 wherein said metal is selected from the group consisting of copper, lead, molybdenum, nickel, tin, zinc and mixtures thereof.

16. The method of claim 15 wherein said metal is selected from the group consisting of lead, tin and mixtures thereof.

17. The method of claim 13 wherein from about 0.05 to about 1.5 wt. % of said metal salt of a fatty acid is added to said basestock.

18. A method for preparing a metal salt of a fatty acid-dimethyl sulfoxide complex which comprises the steps of
  (a) combining a metal salt of a fatty acid with an excess of dimethyl sulfoxide to form a mixture,
  (b) heating the mixture formed in (a) at a temperature between 50° and 130° C. for from about 1 to about 4 hours,
  (c) cooling the mixture formed in (c) to a temperature between about 10° C. and about 25° C., and
  (d) recovering said metal salt of a fatty acid-dimethyl sulfoxide complex.

19. The method of claim 18 wherein said metal is selected from the group consisting of Groups IB, IIB, IVB, VIB, VIIB, VIIIB and mixtures thereof.

20. The method of claim 19 wherein said metal salt of a fatty acid is selected from the group consisting of metal laurates, metal oleates, metal palmitates or metal stearates.

21. The method of claim 20 wherein said metal salt of a fatty acid comprises a metal palmitate.

22. The method of claim 21 wherein said metal is selected from the group consisting of copper, lead, molybdenum, nickel, tin, zinc, and mixtures thereof.

23. The method of claim 22 wherein said metal is selected from the group consisting of lead, tin and mixtures thereof.

24. The method of claim 20 wherein from about 0.05 to about 1.5 wt. % of said metal salt of a fatty acid is added to an engine lubricating oil.

25. A method of improving the wear performance of an internal combustion engine by lubricating said engine with a lubricating oil comprising a major amount of a lubricating oil basestock and a minor amount of at least one metal salt of a fatty acid that is complexed with dimethyl sulfoxide, wherein said metal is selected from the group consisting of Groups IB, IIB, IVB, VIB, VIIB, VIIIB and mixtures thereof.

26. The method of claim 25 wherein said metal salt of a fatty acid comprises a metal palmitate.

27. The method of claim 26 wherein said metal is selected from the group consisting of copper, lead, molybdenum, nickel, tin, zinc and mixtures thereof.

28. The method of claim 27 wherein said metal is selected from the group consisting of lead, tin and mixtures thereof.

29. The method of claim 25 wherein from about 0.05 to about 1.5 wt. % of said metal salt is present in said lubricating oil.

30. The method of claim 25 wherein said metal salt of a fatty acid has at least 11 carbon atoms.

* * * * *